US00PP16045P2

(12) United States Plant Patent
Knudsen

(10) Patent No.: US PP16,045 P2
(45) Date of Patent: Oct. 18, 2005

(54) ***DAHLIA* PLANT NAMED 'COCOS'**

(50) Latin Name: ***Dahlia* (hybrid)**
Varietal Denomination: Cocos

(75) Inventor: Jan Skjold Knudsen, Odense N (DK)

(73) Assignee: Dalina APS, Odense N (DK)

( * ) Notice: Subject to any disclaimer, the term of this patent is extended or adjusted under 35 U.S.C. 154(b) by 0 days.

(21) Appl. No.: 10/808,317

(22) Filed: Mar. 25, 2004

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—Foley & Lardner, LLP

(57) ABSTRACT

A new and distinct cultivar of *Dahlia* plant named 'Cocos' characterized by its yellow ray floret color, RHS 2B; compact plant habit; and vigorous growth habit.

3 Drawing Sheets

Genus and species of the plant claimed: *Dahlia* (hybrid). Variety denomination: 'Cocos'.

BACKGROUND OF THE INVENTION

The present Invention relates to a new and distinct cultivar of *Dahlia* plant, botanically known as *Dahlia* (hybrid), and hereinafter referred to by the name 'Cocos'. The new cultivar 'Cocos' is a product of a planned breeding program and was selected by the Inventor, Jan Skjold Knudsen, in Fyn, Denmark. The new cultivar 'Cocos' originated from a cross made by the Inventor between the *Dahlia* cultivar designated 'Malaysia' (unpatented) as the female parent and the *Dahlia* cultivar designated 'Tonga' (unpatented) as the male parent.

Asexual reproduction by cuttings of the new variety in Fyn, Denmark has demonstrated that the combination of characteristics as described herein for 'Cocos' are firmly fixed and are retained through successive generations of asexual reproduction. The new variety reproduces true to type.

BRIEF DESCRIPTION OF THE INVENTION

'Cocos' has not been tested under all available environmental conditions and the phenotype may vary with variations in environmental conditions such as temperature, light intensity, day length and humidity, without a change in genotype of the plant.

The following traits have been repeatedly observed and are determined to be the unique characteristics of 'Cocos'. The following characteristics in combination distinguish 'Cocos' as a new and distinct cultivar:

1. Yellow ray floret color, RHS 2B;
2. Compact plant habit; and
3. Vigorous growth habit.

Side-by-side comparisons between the new *Dahlia* cultivar 'Cocos' and the parental cultivars, 'Malaysia' and 'Tonga', were conducted by the Inventor in Fyn, Denmark. 'Cocos' differs from the female parental cultivar 'Malaysia' primarily in ray floret color. 'Cocos' has yellow ray florets, RHS 2B, whereas the ray floret color of 'Malaysia' is light purple, RHS 75A to 75B. The leaves and inflorescence of 'Malaysia' are smaller than the leaves and inflorescence of 'Cocos'. 'Cocos' differs from the male parental cultivar, 'Tonga', primarily in ray floret color. 'Cocos' has yellow ray florets, RHS 2B, whereas the ray floret color of 'Tonga' is yellow-orange, RHS 44A. 'Tonga' also has disc florets in which the anthers show through the unopened disc floret corollas.

Of the commercial cultivars known to the Inventor, the most similar in comparison to the new *Dahlia* cultivar 'Cocos' is the female parental cultivar 'Malaysia' (unpatented).

BRIEF DESCRIPTION OF THE DRAWINGS

The accompanying color photographs illustrate the overall appearance and details of inflorescence form color and structures of the new cultivar, showing the colors as true as it is reasonably possible to obtain in color reproductions of this type. Colors in the photographs may differ slightly from the color values cited in the detailed botanical description, which accurately describe the actual colors of the new *Dahlia*.

The first photograph is a side view of a typical flowering plant of 'Cocos' as grown in an 11 cm pot.

The second photograph is a top view of a typical flowering plant of 'Cocos'.

The third photograph is a close-up of the inflorescence of 'Cocos'.

DETAILED BOTANICAL DESCRIPTION

The following observations, measurements and values describe 8 week old plants grown in 11 cm containers under commercial conditions. Plants described were grown in a greenhouse in Fyn, Denmark with average day temperatures of 18° C. to 25° C., and night temperature of 16° C. All color references are measured against The Royal Horticultural Society (R.H.S.) Colour Chart. Colors are approximate as color depends on horticultural practices such as light level and treatment rate, among others, without however any variance in genotype.

Plant:

*Form.*—Globular, upright.
*Height.*—15 cm.
*Spread.*—18 cm.
*Natural flowering season.*—Summer to fall.

*Crop time.*—After rooting, about 10–12 weeks are required to produce finished flowering plants in 11 cm pots.

*Plant vigor.*—Virorous.

*Root structure.*—Fibrous.

*Stem.*—Yellow-green RHS 144B, glabrous; diameter 10–12 mm.

*Lateral branches.*—12–14 in quantity; 7–10 mm diameter; 10 cm in length (including inflorescence); yellow-green, RHS 144C.

*Internode length.*—3 cm.

Foliage:

*Leaves.*—Quantity: 4–5 pairs per lateral branch. Arrangement: Opposite, decussate. Length: Up to 10 cm, generally about 5 cm. Width: 6–7 cm, generally about 3–4 cm. Shape: Elliptical, acuminate tip, decurrent base, crenate margin. Texture: Glabrous. Color: Young leaf upper side: green RHS 135 A; young leaf underside gray-green RHS 189 C; mature leaf upper side: green, RHS N 134 A; mature leaf under side: gray-green RHS 189 C.

*Compound leaves.*—Quantity: Very few, about 10 of 60 leaves on plant are compound leaves. Arrangement and shape: Near flowers, ternate with one apical leaflet larger than the two basal leaflets. Size: Apical leaflet (about 4 cm length×3 cm width) and with petiolule 5 to 10 mm in length; basal leaflets (2 cm length×1 cm width) and are sessile to the rachis. Venation: Vein color upper side 135C, vein color under side 144A. Petiole: 4–5 cm in length; 5–8 mm in diameter; color RHS 144A.

Inflorescence:

*Arrangement.*—Composite inflorescences in leaf axils.

*Inflorescence type.*—Capitulum.

*Inflorescence height.*—3–4 cm.

*Inflorescence width.*—6–7 cm.

*Flowering habit.*—Upright.

*Quantity of inflorescences.*—2–3 per lateral stem.

*Inflorescence longevity.*—7 days on the plant.

Bud:

*Quantity.*—2–3 per lateral stem; (buds continue to develop when dead inflorescences are removed).

*Shape.*—Globular.

*Size.*—Up to 2 cm in length, 1 cm diameter.

*Color.*—RHS 144C.

Florets:

*Appearance.*—Disc, tubular to single, floret (lanceolate to rounded tip); ray, single fused floret (almost circular, to involute at the sides and with rounded tip).

*Shape.*—Disc, lanceolate; ray oval, involute.

*Number.*—About 20 disc florets and 70 ray florets per capitulum (depending on light and temperature conditions).

*Length.*—Disc 3–4 mm, ray 25–30 mm.

*Width.*—Disc 3 mm, ray 25–30 mm.

*Diameter.*—Disc 2–3 mm.

*Margin.*—Entire.

*Apex.*—Rounded.

*Color.*—Disc: Upper side: transparent yellow, RHS 2D, letting the color of the anthers come through from green, yellow, RHS 1B, before anthesis, to orange, RHS 14A, at anthesis; Ray: Upper side, yellow RHS 2 B (mature and immature), under side yellow, RHS 2 C (both mature and immature).

Phyllaries:

*Length.*—3 mm.

*Width.*—5 mm.

*Margin.*—Entire.

*Base.*—Fused.

*Apex.*—Rounded.

*Color.*—Immature upper side RHS 138A; immature under side RHS 143D with stripes RHS 143A; mature upper side RHS 137A; under side RHS 191B with stripes RHS 143A.

Calyx: 3 mm length, 17 mm diameter.

Peduncle: 4–6 cm length, 3 mm diameter; strength: strong; color RHS 144C.

Reproductive organs:

Androecium:

*Location.*—Disc florets only.

*Anthers.*—4 mm in length, RHS 23B.

*Pollen.*—RHS 14A.

Gynoecium:

*Location.*—Disc and ray florets.

*Pistils.*—1 per disc floret, 15 mm length.

*Stigma.*—RHS 14A.

*Style.*—9 mm length, RHS 14A.

*Ovary.*—RHS 150B.

Temperature tolerance: High tolerance to 35° C.; low tolerance to 0° C.

I claim:

1. A new and distinct cultivar of *Dahlia* plant named 'Cocos', as described and illustrated herein.

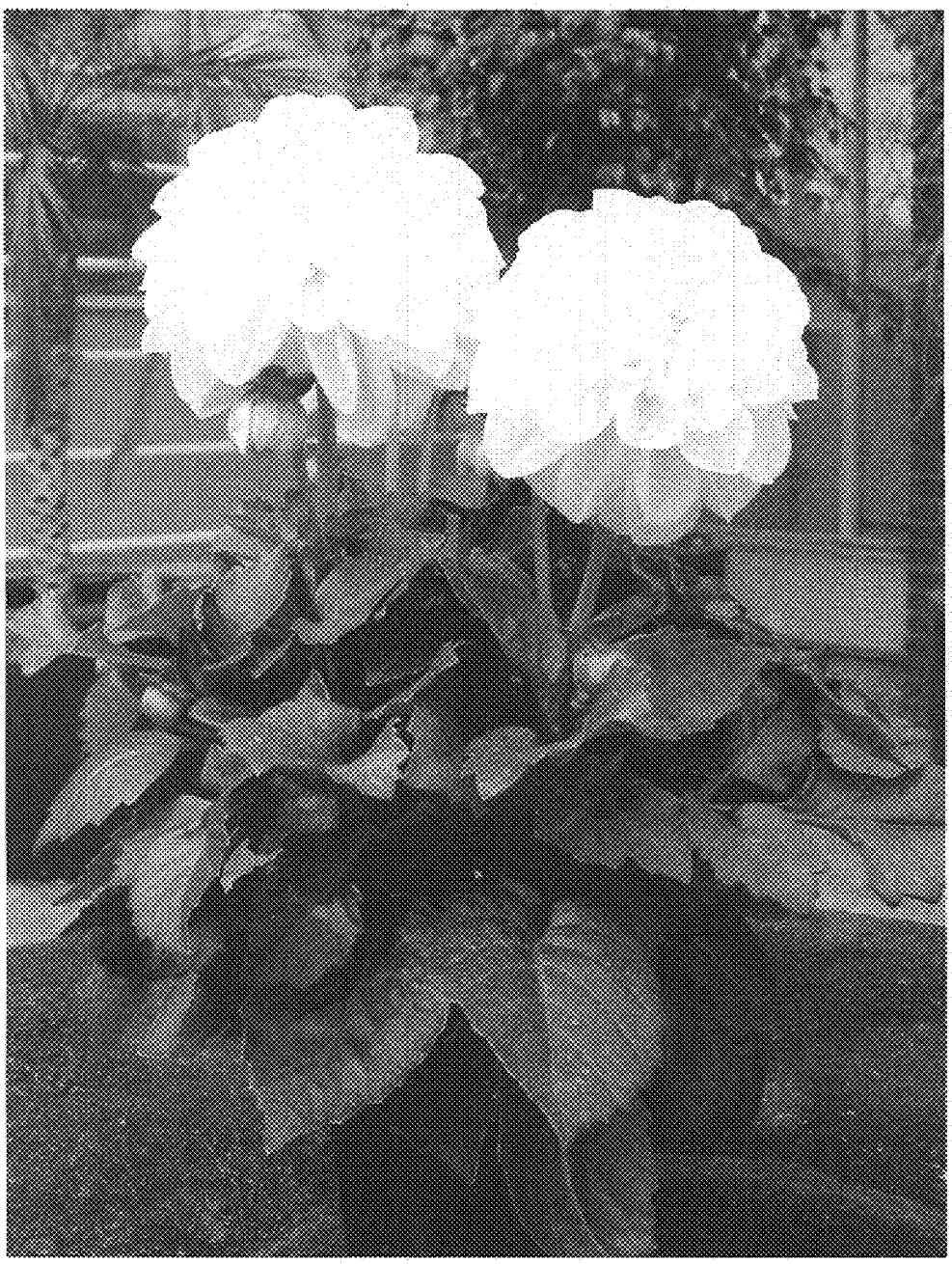

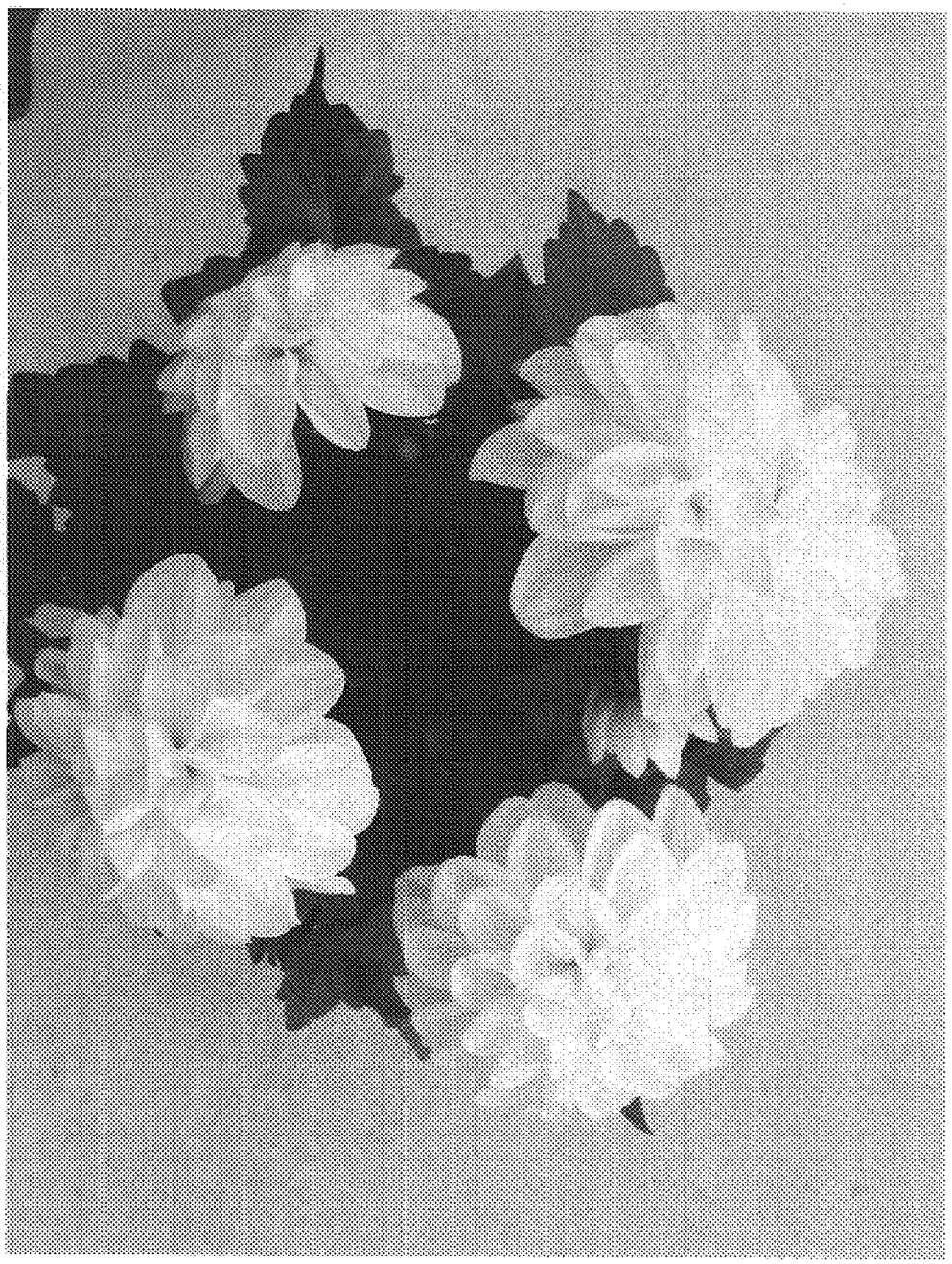

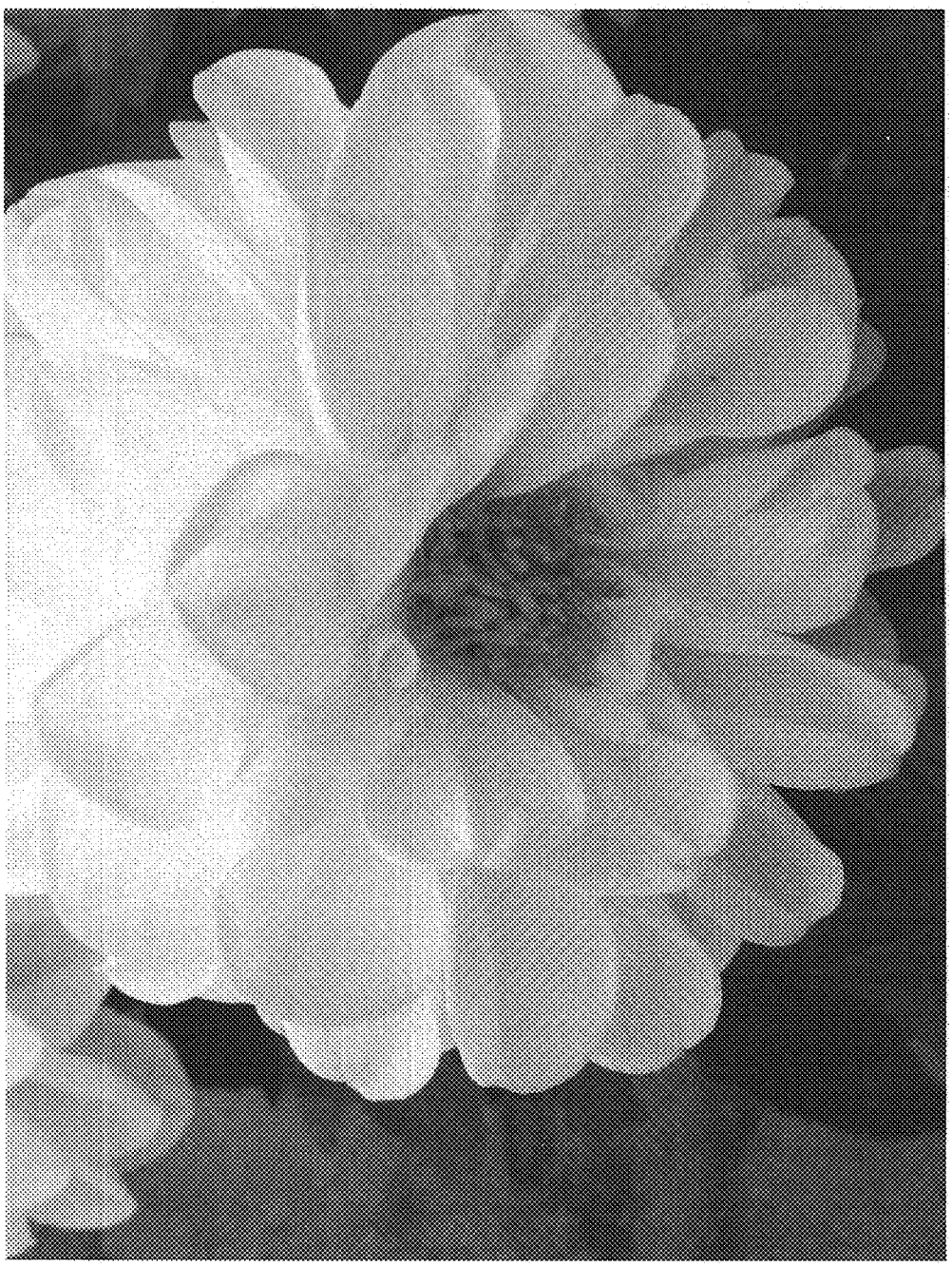

* * * * *